United States Patent [19]

Shiomi et al.

[11] Patent Number: 5,100,786
[45] Date of Patent: Mar. 31, 1992

[54] GENE CAPABLE OF ENHANCING S-ADENOSYL-L-METHIONINE ACCUMULATION AND PROCESS FOR PRODUCING S-ADENOSYL-L-METHIONINE USING THE SAME

[75] Inventors: Naofumi Shiomi; Hideki Fukuda, both of Takasago, Japan

[73] Assignee: Kanegafuchi Kagaku Kogyo Kabushiki Kaisha, Osaka, Japan

[21] Appl. No.: 288,890

[22] Filed: Dec. 23, 1988

[51] Int. Cl.⁵ .............. C12P 13/04; C12N 15/54; C12N 15/81
[52] U.S. Cl. .................. 435/106; 435/172.3; 435/193; 435/224; 435/252.3; 435/255; 435/320.1; 536/27; 535/60; 535/69
[58] Field of Search .............. 435/69.9, 69.1, 193, 435/224, 172.3, 255, 256, 320.1; 935/60, 69; 536/27

[56] References Cited

U.S. PATENT DOCUMENTS 3,962,034 6/1976 Tsuchida et al. ............. 195/28 N
4,546,082 10/1985 Kurjan et al. ................ 435/172.3

FOREIGN PATENT DOCUMENTS 58-146274 8/1983 Japan .

OTHER PUBLICATIONS

Thomas et al., 1988, Mol. Cell. Biol. 8:5132, SAM2 encodes the 2nd Methionine S-Adenosyl.
Thomas et al., 1987, J. Biol. Chem. 262:16,704, SAM1, the Structural Gene of One of the S-Adenosylmethionine Synthetases in S, cerevisiae.
Shiomi et al., 1988, Cloning of a Gene for S-adenosylmethionine synthesis in S. cerevisiae. Appl. Microbiol. Bio. Tech. 29: 302-304.
Journal of Bacteriology, vol. 121, No. 1, pp. 267-271 (1975).

Primary Examiner—Richard A. Schwartz
Assistant Examiner—John L. LeGuyader
Attorney, Agent, or Firm—Armstrong, Nikaido, Marmelstein, Kubovcik and Murray

[57] ABSTRACT

A gene which provides resistance to at least one methionine derivative and is capable of enhancing accumulation of S-adenosyl-L-methionine (SAM) in a cell, a hybrid plasmid having the same, a cell transformed with the above hybrid plasmid, and a process for producing SAM using the above cell. According to the present invention, SAM, which has various therapeutic effects, can be producing in a large amount at a low cost.

7 Claims, 5 Drawing Sheets

GENE CAPABLE OF ENHANCING S-ADENOSYL-L-METHIONINE ACCUMULATION AND PROCESS FOR PRODUCING S-ADENOSYL-L-METHIONINE USING THE SAME

BACKGROUND OF THE INVENTION

The present invention relates to a gene concerning S-adenosyl-L-methionine (hereinafter referred to as "SAM"). More particularly, the present invention relates to a gene enhancing an accumulation of SAM in a cell and a process for producing SAM using a cell having the gene.

It has been known that SAM participates in metabolism of fats, proteins, suger chains, and the like, and has effects on the therapies of excessive lipemia, arteriosclerosis, psychosis manifestations such as depression and neuropathic diseases, degenerative arthropathy neuropathic pain, sleeplessness, brain damage, and the like. Therefore, the mass production of SAM is desired.

SAM is a very unstable substance, and decomposes into 5'-methylthioadenosine and the like in a medium, though it is stable in a cell. Therefore, for the mass production of SAM, it is important how to keep SAM in a cell in a high concentration. It is well known that SAM can be accumulated in a high concentration in a cell when the cell is cultured in a medium containing methionine. For example, as to yeast, it is described in Journal of Biological Chemistry 229, 1037 (1957), Journal of Bacteriology 121, 267 (1975), Japanese Examined Patent Publication No. 17118/1977, and the like.

Further, for enhancing the accumulation of SAM to a higher concentration, there are processes in which other substances are added to the medium as well as methionine. There are exemplified, for instance, a process in which an amino acid not having sulfur atom is added (Japanese Unexamined Patent Publication No. 28296/1983), a process in which glycine or alanine is added (Japanese Unexamined Patent Publication No. 36397/1983), a process in which a heavy metal ion such as calcium ion or iron ion is added (Japanese Unexamined Patent Publication No. 40095/1983), a process in which a base is added (Japanese Unexamined Patent Publication No. 40096/1983), a process in which an ammonium salt or the like is added (Japanese Unexamined Patent Publication No. 138393/1983), a process in which a substance colouring in ninhydrin reaction is added (Japanese Unexamined Patent Publication No. 146274/1983), a process in which a specific amine is added (Japanese Unexamined Patent Publication No. 152497/1983), a process in which adenylic acid or the like is added (Japanese Unexamined Patent Publication No. 78594/1985), and the like. However, for practicing them industrially, there still remain problems that the content of SAM in a cell is not always increased that it is needed that cells are cultured in the medium containing expensive methionine in a high concentration, and the like.

As to several genera in bacteria, yeast, and the like, cells provided with ethionine-resistance by mutation treatment and the like have been already obtained. However, generally, they were not cells containing SAM in a high concentration, but cells in which the synthesis of SAM from methionine is suppressed because of a low activity of methionine adenosyltransferase (hereinafter referred to as "MAT") and the content of SAM is remarkably low (Mertz et al, Journal of Bacteriology 111, 778-783 (1972)). The above-mentioned cells show ethionine-resistance for the following reason. That is, the inhibition of growth of cells by a methionine derivative is caused through the steps, for instance in case of the methionine derivative being ethionine, that ethionine is converted into S-adenosyl-L-ethionine (hereinafter referred to as "SAE") by MAT, and that the SAE inhibit the methylation of SAM and also inhibit the growth of cells (for instance, Stekol. Advance in Enzymology 15, 369-393 (1963)). In ethionine-resistant cells, since the gene coding for MAT is destroyed by mutation treatment and therefore MAT activity is low, a synthesis of SAE from ethionine is inhibited (for instance, an example as to Escherichia coli, is described in Green et al, Biochemical and Biophysical Research Communication 38, 1120-1126 (1970)). Consequently, ethionine-resistance can be shown. Therefore, in the cells, the synthesis of SAM from methionine is also inhibited and a large amount of methionine is accumulated. In other words, ethionine-resistant cells are cells in which the accumulation of SAM is suppressed.

SUMMARY OF THE INVENTION

As a result of an eager study for increasing the accumulation amount of SAM in a cell in culturing yeast, it has been now found that, when a plasmid DNA carrying a gene providing a methionine derivative-resistance transformed into a cell by means of a gene recombination, though the greater part of the cells suppress the accumulation of SAM, some of them can accumulate SAM in a high concentration in the cells. Thus, the present invention has been accomplished.

The gene found by the present inventors (hereinafter referred to as "SAM gene") carries a gene which enables the cell to accumulate SAM in a large amount though the gene also provides the cell with ethionine-resistance. The gene differs from conventional ethionine-resistant cells in the principle. The reason why SAM gene provides resistance to ethionine is not clear. However, the gene is closely concerned with the capacity of SAM accumulation in a cell and can cause an accumulation of SAM in a high concentration in the cell.

That is, according to the present invention, there are provided a gene which provides resistance to at least one methionine derivative and is capable of enhancing accumulation of S-adenosyl-L-methionine (SAM) in a cell, a hybrid plasmid having the above gene, a cell transformed with the above hybrid plasmid, and a process for producing SAM by culturing the above cell and collecting the accumulated SAM.

BRIEF DESCRIPTION OF THE DRAWINGS

FIG. 1 (A) shows a restriction enzyme map of a plasmid pYSMH 1.

FIG. 1 (B) shows a DNA fragment (restriction enzyme map) of SAM gene which is contained in the above plasmid.

DETAILED DESCRIPTION

Hereinafter, the present invention is explained in details as to a process for obtaining SAM gene and a process for accumulating SAM by SAM gene in a cell.

[Process for obtaining SAM gene]

For obtaining SAM gene, a DNA fragment taken out from a DNA donor is inserted in a vector plasmid, and the plasmid is transformed into on an yeast to be a host. Then, the yeast is screened to give an yeast carrying SAM gene.

In the present invention, the term "DNA donor" means a cell, a microorganism or the like which serves as a source of DNA to be inserted in a vector. When DNA synthesized from RNA as a template is inserted in a vector, "DNA donor" is a cell, a microorganism or the like which is the source of the RNA.

Examples of the DNA donors are, for instance, cells derived from any animals and plants; a fungi belonging to genus *Penicillium, Aspergillus, Fusarium, Gibberella, Memnoniella, Nigrospora, Trichoderma, Monascus, Stemphyrium, Oosupora, Botrytis*, or the like; a bacterium belonging to genus Achromobacter, Bacillus, Brevibacterium, Corynebacterium, Escherichia, Micrococcus, Pseudomonas, Salmonella, Staphylococcus, or the like; an yeast belonging to genus Candida, Saccharomyces, Shizosaccharomyces, Pichia, Debaryomyces, Rhodotorula, Torulopusis, Hansenula, Kloekera, Brettanomyces, Cryptococcus, Kluyveromyces, Rhodosporidium, or the like; and the like.

A DNA fragment can be obtained from a DNA donor by means of a conventional process. For instance, by extracting chromosomal DNA and cutting it with a suitable restriction enzyme, a DNA fragment is obtained from a DNA donor. For example, in an eucaryotic cell, an improved phenol method (Biochimica et Biophysica Acta 72, 619–629 (1963)), a process in which after extracting a messenger RNA (mRNA) in a DNA donor, a single-strand cDNA is prepared with a reverse transcriptase and then doublestrand DNA is obtained from the cDNA (for instance, as to an eucaryotic cell, see Molecular Cloning, 187–247 (1982), published by Cold Spring Harbor Laboratory), and the like are employed for obtaining DNA fragment from DNA donors.

The term "host" is a living cell into which a recombinant molecule of DNA (hybrid plasmid) is to be transformed.

As the host, cells derived from any animals, plants and microorganisms can be employed in the present invention. For instance, an yeast belonging to genus Candida, Saccharomyces, Shizosaccharomyces, Pichia, Debaryomyces, Rhodotorula, Torulopusis, Hansenula, Kloekera, Brettanomyces, Cryptococcus, Kluyveromyces, Rhodosporidium, or the like is preferably employed. Among them, an yeast having comparatively large vacuales is more preferable.

The term "vector" is a DNA carring foreign DNA to a host. As a vector used in the present invention a vector which is fit for the host and can make DNA fragment from a DNA donor express in the host may be suitably selected.

As a vector derived from genus *Saccharomyces*, for example as a vector of *Saccharomyces cervisiae*, there can be employed any vector having at least one DNA sequence which is essential to autonomious replication independent from the host chromosome (such DNA sequence hereinafter referred to as "ars"), e.g. plasmid YCp, plasmid YRp and the like; a vector having at least one replication origin (ORI) derived from 2 μm plasmid DNA, e.g. plasmid YEp and the like; a vector having at least one centromere region (CEN) of the third chromosome in yeast; a vector not containing ars among the above, e.g. plasmid YIp; a vector having at least one replicator derived from mitochondria (rep 1, rep 2, rep 3); an autoreplicable linear vector obtained by cutting a circular vector in yeast with a restriction enzyme to give a linear vector, and adding the end region of ribosome DNA in Tetrahymena to the both ends of the linear vector; a linear vector in which the above autoreplicable linear vector is substituted with telomere of yeast chromosome at its one end; a cosmid vector in which inserted glairy end of λ phage DNA is inserted into a circular vector; a vector in which the above-mentioned vector is improved by using recombinant DNA technique; or the like. When the host is an yeast belonging to genus Saccharomyces, the above-mentioned vectors can express in almost all cases. Moreover, the above vectors can also express in a host other than Saccharomyces, e.g. genus Shizosaccharomyces and the like. In these cases, the above-mentioned vectors may be used in other genera.

As to genus Candida, for example, in Candida maltosa, a vector having ars (Koubonozoshokutoriyou (Growth and Use of Yeast), 27-37, published by Gakkaishuppan center) or the like may be used.

Recently, as to genus Hansenura, for example, host-vector system of *Hansenura polyfoma* has been developed (Nikkeibaioteku (Nikkei bio tech), No. 140, 8), which may be used. Also, when a host in which the above vectors of genus Saccharomyces, genus Candida or genus Hansenura do not express is used, according to the same process for preparing the above-mentioned vectors, a vector may be prepared after CEN, ars, ORI or the like derived from the host is taken out.

The vector and the DNA fragment can be combined by means of a conventional process, for example, a process in which a DNA ligase derived from T4 phages is used (Gellet et al, Proceeding of Nucleic Acid Research 2, 875-888 (1971) (hereinafter, the DNA obtained by combining a vector and a DNA fragment derived from a DNA donor referred to as a "hybrid plasmid")).

The hybrid plasmid can be transformed into a host (hereinafter, the cell in which the hybrid plasmid is transformed referred to as "transformant") by means of known processes such as a process for transforming DNA into an yeast made to be a protoplast with a cell-wall digesting enzyme in the presence of calcium ion and polyethylene glycol (Proceedings of the National Academy of Sciences of the U.S. of America 75, 1929 (1978), a process in which an yeast treated with a surface active agent is used (Showa 57 nendo Nippon Nogeikagakukai taikaiyoshishu, 568 (1982)), and a process in which an yeast treated with an alkali metal or thiol (Journal of Bacteriology 153, 163 (1983)); Agricultural and Biological Chemistry 47, 1691 (1983)). A cell carrying SAM gene can be selected from yeast cells into which the hybrid plasmid is transformed by culturing the yeast in a medium not containing any methionine derivative, culturing the yeast in an agar medium containing at least one methionine derivative, and selecting an yeast showing a higher resistance to the methionine derivative than that the parent yeast originaly had (hereinafter referred to as "first selection"). The term "higher resistance" means that growth rate is faster when cells are cultured in media containing methionine derivative in the same concentration. In general, when cells are cultured in a medium containing a methionine derivative in such a concentration that the host itself cannot grow, a colony which grows can be determined to have resistance higher than that of the host.

As a methionine derivative used in the present invention, any methionine derivative can be used. Examples of the methionine derivatives are, for instance, L-ethionine, L-selenomethionine, L-methionine hydroxamate, L-trifluoromethionine, L-methionine methyl ester, L-methionine ethyl ester, L-N,N-formyl-methionine, L-N-acetyl-mehionine, and the like. Also, racemates of the above-mentioned methionine derivatives can be used. The concentration of methionine used may be determined depending on the host used. For example, in case the host is an yeast, e.g. genus Saccharomyces, ethionine is used in a concentration of 10-100 μg/ml and selenomethionine is used in a concentration of 1-10 μg/ml. Their concentration can be suitably selected in the above range.

Further, after culturing each selected transformant in a medium containing a methionine derivative, the SAM concentration is measured as for each selected transformant. As a result, transformants can be classified into two types. One is a class, to which the most part of the resistant cells belong, of the transformant which remarkably suppresses SAM content in the cell (hereinafter referred to as "class 1"). The other is a class, to which few resistant cells belong, of the transformant which remarkably enhances SAM content in the cell (hereinafter referred to as "class 2"). Since SAM gene is contained in cells belonging to class 2, yeast carrying SAM gene can be obtained when any yeast belonging to class 2 is isolated.

One of the characteristics of the present invention is the above selection procedure. That is,
(1) After a hybrid plasmid is transformed into a cell, the cell is once cultured in a growth medium,
(2) The cells which can enhance the concentration of SAM to a high concentration are further selected from the cells which indicate the resistance to a methionine derivative.

According to the procedure (1), pools of SAM in the cells are enhanced and they are formed, and they can be provided with the resistance to methionine derivatives.

When cells into which hybrid plasmids are introduced are directly cultured in an agar medium containing at least one methionine derivative, and the transformant, which shows a resistance to a higher concentration of the methionine derivative than that of the parent strain is selected, only class 1 transformants in which the SAM content is remarkably suppressed can be obtained. Further, even when the cells are treated according to the above procedure (1), the majority of cells which are transformants belonging to class 1. Only after the treatment according to the above procedure (2), the SAM gene of the present invention can be obtained. That is, even if a transformant indicates the resistance to methionine derivatives such as ethionine, it does not mean that the transformant can accumulate SAM in a high concentration. When the procedures (1) and (2) in the present invention are not carried out, the methionine derivative-resistant cell is the cell in which the SAM content is suppressed.

The SAM gene can be extracted and purified in a usual manner from the yeast cell into which the SAM gene is introduced, which are obtained in the above process. For example, in an yeast, a process in which a shuttle vector with *E. coli* is used as a vector, and the plasmid extracted from the yeast is transferred into *E. coli*, the plasmid is amplified, and a purification is carried out by using ultracentrifugal separation of cesium-chloride is usually used.

The restriction enzyme map of the gene can be made by the appropriate digestion of the purified plasmid with various restriction enzymes.

Process for accumulation of SAM by SAM gene in a cell

In order to accumulate SAM in a high concentration in a cell by using the SAM gene which is obtained by the above process, the hybrid plasmid which was obtained by inserting the SAM gene appropriately taken out into the vector, may be transformed into a host cell and the host cell may be cultured by a usual culture method. For example, when an yeast is used as the host, a medium which suitably contains a carbon source, a nitrogen source, an inorganic salt or other organic nutrients can be used.

Examples of the sources of carbon are, for instance, saccharides such as glucose, sucrose, maltose, fructose, lactose, starch and a hydrolysate of starch; alcohols such as methanol, ethanol, propanol, butanol, glycerol, sorbitol and a higher alcohol; organic acids such as succinic acid, citric acid, lactic acid, tartaric acid, acetic acid, propionic acid, butyric acid, gluconic acid, fumaric acid and benzoic acid; alkali salts formed with these organic acids; esters formed with the above-mentioned saccharides or alcohols; hydrocarbons such as alkanes having 1 to 25 carbon atoms and alkenes having 1 to 25 carbon atoms; and the like.

Examples of the sources of nitrogen are, for instance, ammonium salts such as ammonium nitrate, ammonium sulfate, ammonium chloride, ammonium succinate and ammonium citrate; nitrates such as sodium nitrate and potassium nitrate; aqueous ammonia; ammonia gas; urea; amino acids; peptides; substances related to nucleic acids; and the like.

Examples of the inorganic salts are, for instance, phosphates such as calcium phosphate, sodium phosphate and potassium phosphate; potassium salts such as potassium chloride; calucium salts such as calcium chloride; magesium salts such as magnesium sulfate and magnesium chloride; sodium salts such as sodium chloride and sodium carbonate; manganese salts such as manganese sulfate and manganese chloride; heavy metal salts such as chlorides of iron, zinc, copper and cobalt, sulfates thereof and nitrates thereof; and the like. Besides, examples of the organic nutrients, for instance, amino acids such as glycine, alanine, serine, threonine, aspartic acid, glutamic acid, ornithine, proline and tyrosine, peptides such as peptone, casamino acid, glycylglycine, alanylalanine and alanylglycine; vitamins such as biotin and pantothenic acid; natural substances such as yeast extract, meat extract, malt, malt extract, corn steep liquor, soybean powder, rice bran, a hydrolysate of soybean protein, a hydrolysate of casein, substances related to nucleic acids such as uracil, cytosine, thymine, adenine, purine, nucleosides consisting of the above base and ribose or deoxyribose, monophosphates thereof, diphosphates thereof, triphosphates thereof and phosphoric esters thereof; 1,2,4-triazoles such as 3-amino-1,2,4-triazole; and the like.

Even if the medium does not contain methionine, a large amount of SAM can be accumulated in a cell.

However, in order to accumulate SAM in a still higher concentration in the cell, methionine may be contained in growth media. The concentration of methionine to be added to a medium is preferably not more than 50 mmol/l, and more preferably, not more than 20 mmol/l. As the methionine, L-methionine or D,L-methionine can be used. And any other methionine source which contains methionine and does not have very bad influence on the growth of the cell, for instance, commercially available reagent, media fermented by microorganism, concentrate thereof, partially purified standard reagent thereof, crude product of methionine which is synthesized chemically or enzymatically, and the like.

SAM can be accumulated in a high concentration by either aerobic or anaerobic culture. Therefore, both culture method may be used. However, in order to incease the yield of SAM per carbon source, it is preferable to carry out the culture at pH 3 to 8 for 1 to 5 days at a temperature of 15° to 40° C. aerobically by, for example, aerative stirring. Further, in order to increase the yield of SAM per methionine, it is preferable, for example, to carry out the culture so that the medium contains as many cells as 100 g of dry cells per 1 l of medium, or to carry out the culture with removing only cells continuously by using a centrifuge or a filter.

In the present invention, the transformed SAM gene can be maintained in the host cell according to the stability of the vector. In order to maintain the SAM gene in the host more stably, a vector having a high copy number, for example, in an yeast, a YEp vector, or a vector having a large fragment of 2μm, for example, pYX (Proceedings of National Academy of Sciences of the U.S. of America 72, 4085-4089 (1975)), pJB 219 (Cell Biology 12, 39-44 (1975)), and the like can be used. Also, the SAM gene can be incorporated into a chromosome by using a YIp vector. Further, recombinant yeast may be grown selectively over non-recombinant yeast. For the selective growth, for example, a selectable gene (hereinafter referred to as "marker gene") is inserted in the vector and the yeast is cultured in a medium in which the marker gene is effective.

As the marker gene, any gene which expresses in a host cell can be used. Examples of the marker gene are, for example, a drug resistance gene, a gene for biosynthesis of an amino acid, a gene for biosynthesis of a nucleic acid, a gene for biosynthesis of a vitamin, a gene for biosynthesis of other substances in a living body, and the like. As the drug resistance gene, for example, the resistance gene to G 418 (commercially available under the trade name Geneticne) (Jimenez et al, Nature 287, 869 (1980)), the resistance gene to a heavy metal or methyl glyoxal (Murata et al, Applied and Environmental Microbiology 50, 1200 (1985)) and the like are known.

Further, since the SAM gene itself is a marker gene which is resistant to methionine derivatives, cells may be cultured in a medium containing a methionine derivative, for example about 50 mg/l of ethionine. In this case, not only the hybrid plasmid is maintained extremely stably, but also is the total SAM content and adenosyl ethionine (hereinafter referred to as "SAE") in the cell can be remarkably increased to be nearly 4 times the total amount thereof in case of not containing ethionine although the reason is not known.

Further, in order to enhance the effect of the SAM gene, a gene to express the SAM gene strongly (hereinafter referred to as "promoter") may be inserted. Examples of the strong promoters are, for instance, a promoter of a gene coding for an enzyme highly expressed in a cell, for instance, a gene coding for an enzyme for glycolysis or the like, e.g. a promoter of a gene coding for glucokinase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, enolase, 3-phosphoglycerate kinase, glyceraldehyde-3-phosphate anhydrase, or the like. Further, as promoters, expression of which can be controlled by the kind of medium employed, promoters of gene coding for galactose, phosphatase, and the like can be exemplified.

The SAM obtained by the above-mentioned process may be purified by a method usually used. For extracting SAM from cells, methods using an extracting reagent such as perchloric acid, hydrochmoric acid, sulfuric acid, formic acid or acetic acid, a method using a surface active agent such as an anionic surface active agent, cationic surface active agents or a nonionic surface active agent, a method using an organic solvent such as acetone or toluene, a method using hot water or the like may be used. Also, disruption methods in which a membrane disruption treatment is carried out by freezing, drying, mechanical disruption, ultrasonic disruption, and the like may be also used to extract SAM from cells.

For purifing the above extract, a method for separation and purification by an ion exchange resin such as an anionic exchange resin, a cationic exchange resin or a nonionic exchange resin, a method for separation and purification by a gel filtration, or the like may be used.

As the effect of the present invention, the following (1) to (5) can be pointed out.

(1) By using yeast transformed with the gene of the present invention, a large amount of SAM can be accumulated in cells even when cells are cultured in a medium not containing methionine.

(2) By using yeast transformed with the gene of the present invention, when cells are cultured in a medium containing methionine, SAM content in cells is further increased. Even this case, the required amount of methionine is very small, and therefore it is economical.

(3) When ethionine is contained in a medium, a still higher concentration of SAM and SAE in cells can be achieved.

(4) SAM can be produced in a large amount, accompanying with a large amount accumulation of SAM in cells.

(5) When the gene of the present invention is transformed into yeast having high SAM content, a strain of yeast capable of accumulating SAM at an extremely high amount in the cell can be created.

Hereinafter, the present invention is more specifically explained by means of Examples. At present, in yeast, only laboratory storage strains of Saccharomyces cervisiae are approved as the host of recombinant DNA (Guidelines for recombinant DNA experiments, revision of 24th August, 1985). Therefore, in Example, although only cases of using genus Saccharomyces as a host are explained in detail, the basic concept of the present invention is to enhance the accumulation of SAM, and it is needless to say that in hosts other than genus Saccharomyces the present invention can be also carried out and that the present invention is not limited to Examples.

Besides, vector plasmid DNA YEp13, which is used in Examples as a vector, and E. coli DH1 and C600, which are used as hosts, are available from American Type Culture Collection through deposit numbers ATCC37115, ATCC33849 and ATCC23724, respectively. Further, DKD-5D-H/pYSMH 1 which was obtained in the present invention, is available from Fermentation Research Institute Agency of Industrial Science and Technology, Japan through a deposit number FERMBP-1629.

EXAMPLE 1

(a) Preparation of a gene bank of yeast

Yeast of *Saccharomyces cervisiae* DKD-5D-H (a, trp 1, leu 2 - 3, leu 2 - 112, his 3) was used as an example of DNA donor. That is, DKD-5D-H strain was cultured while shaking in 1 l of YPD medium (2 % peptone, 1% yeast extract and 2% glucose) at 30° C. for 24 hours until stationary phase. After collecting the yeast cells, chromosomal DNA was extracted according to the method of Saito Miuro (Biochemica et Biophysica Acta 72, 619-629 (1963)). That is, the cells were suspended in a buffer solution (pH 8.0) which contains 1M sorbitol, 14 mM mercaptoethanol and 50 mM potassium phosphate to give a suspension containing 0.2 g of cells in 1 ml of the buffer solution. To the above suspension, the cellwall digesting enzyme Zymolyase 100 T (made by Seikagaku Kogyo Co., Ltd.) was added so as to give the enzyme concentration of 0.1 mg/m±, and the solution was allowed to stand for 1 hour at 30° C. After adding 10 % sodium dodecyl sulfate (hereinafter referred to as "SDS") thereto and disrupting the cells completely by allowing the cell suspension to stand at 60° C. for 15 minutes, the suspension was cooled to 4° C. After being purified with a mixture of phenol-chloroform (1 : 1 by volume) several times, precipitated DNA was rooled up with a glass rod while adding cooled ethanol (−20° C.) to give 2 mg of chromosomal DNA.

Then, vector plasmid DNA YEp 13 was purified from *E. coli* C 600 carrying plasmid DNA YEp 13 (such *E. coli* hereinafter referred to as "C 600/YEp 13"). The plasmid DNA YEp 13 contains plasmid DNA pBR322 having ampicillin and tetracycline resistance genes derived from *E. coli*, a part of 2 μm plasmid DNA derived from yeast and a gene (leu 2) of leucine derived from yeast chromosomal DNA. That is, C 600/YEp 13 was cultured in 1 l of L-medium (pH 7.2; 1% peptone, 0.5% yeast extract, 0.1% glucose, and 0.5% sodium chloride). When measured OD (610 nm) value indicated 0.5–0.6, chloramphenicol was added thereto so as to give a final concentration of 150–200 μg/ml. The culture was further continued at 37° C. for 15 hours. After being collected and washed, cells were disrupted with lysozyme and SDS and the supernatant was obtained by centrifugation at 35000 r.p.m. for 1 hour. After equivalent volume of a mixture of phenol-chloroform (1:1 by volume) was added to the supernatant, the mixture was stirred gently and was centrifuged (1000 r.p.m., 10 min) to remove proteins and the like, and then was treated with a ribonucleic acid digesting enzyme at 37° C. for 3 hours. Cesium chloride-ethidium bromide equilibrium density gradient centrifugation was carried out at 3600 r.p.m. for 48 hours to give 1 mg of YEp 13 plasmid.

The previously obtained 2 mg of chromosomal DNA was treated with restriction enzyme Sau3AI for 30 minutes to cut up the DNA partialy, and the obtained DNA fragments were separated by means of agarose gel electrophoresis, and DNA fragment having a molecular weight of about 7.0 kb was extracted from the agarose gel. On the other hand, 1 mg of plasmid YEp 13 was completely cleavaged with restriction enzyme BamHI, and was treated with alkaline phosphatase to prevent self-ligation. Further, both reaction solutions were mixed, a joint reaction was carried out at 4° C. for 16 hours with DNA ligase derived from T4 phage. To the reaction solution, 2-fold volume of cooled ethanol (−20° C.) was added. After allowing it to stand at −20° C. overnight, the precipitate was collected by centrifugation at 10000 r.p.m. for 10 minutes. The precipitate was dissolved in 0.1 ml of 10 mM Trishydrochloride buffer solution (pH 7.5) to give a DNA solution (hereinafter referred to as "hybrid plasmid DNA mixture").

The hybrid plasmid-DNA mixture was transformed into *E. coli* DH1 (F− gyrA96, recAl, relAl, endAl, thi-1, hdsR17, supE44 λ−). The transformation was carried out by means of the calcium method of Cohen et al (Proceedings of the National Academy of Science of the U.S. of America 49, 2110–2114 (1972)). That is , 37° C. When the OD value becomes to be 0.3, the cells were collected, washed once with normal saline solution, and were suspended in Tris-hydrochloride buffer solution (pH 7.6) containing 5 mM magnesium chloride, 0.15M potassium chloride and 0.1M calcium chloride. After being allowed to stand for 1 hour at 0° C., to the suspension was added the hybrid plasmid-DNA mixture. The mixture was allowed to stand for 30 minutes at 0° C., and then was allowed to stand for 25 minutes at 37° C. The mixture was cultured while shaking in L-medium for 2 hours, and was distributed in twenty agar plates of L-medium containing 20 μg/l of ampicillin. As a result, cells transformed with the plasmid (hereinafter referred to as "transformant") grew at least not less than $10^7$ cells. All the transformants were collected, and were purified by the same manner as in the above purification of plasmid DNA YEp 13 to give the hybrid plasmid-DNA mixture (hereinafter referred to as "solution A") in a large amount. Then, the above hybrid plasmid DNA was transformed into yeast cells by means of a process using an alkali metal. Namely, DKD-5D-H strain was cultured while shaking in 40 ml of YPD medium at 30° C. When cells have grown to $2 \times 10^7$ cells in 1 ml of the medium, the cells were collected by centrifugation at 3000 r.p.m. The collected cells were suspended in 2 ml of TE buffer solution (10 mM Tris and 1 mM EDTA, pH 2.5). The suspension was divided into 0.2 ml each, and thereto 0.2 ml of 0.2M lithium acetate was added. After allowing it to stand for 1 hour at 30° C., 0.1 ml of the above-mentioned solution A was added thereto, and the mixture allowed to stand for 30 minutes. After that, 0.5ml of 70% polyethyrene glycol 4000 solution was added thereto, and the mixture was allowed to stand for 1 hour. After allowing it to stand for 5 minutes at 42° C., washing with water and centrifugation were repeated, and the cells were distributed in twenty agar plates of SD+TH (2% glucose, 0.67% yeast nitrogen base w/o amino acid, 20 mg/l of tryptophane and 20 mg/l of histidine). Three days after, all growing colonies were collected.

By the above-mentioned procedure, transformants of yeast coding all informations of chromosomal DNA in yeast, so-called a gene bank of yeast was obtained. (b) Preparation of a gene which provides resistance to methionine derivatives and is capable of enhancing the SAM content in a cell.

The above obtained gene bank of yeast was distributed in an agar plate of SD+TH medium containing 50 μg/ml ethionine at $10^5$ cells per plate. Three days after, cells providing resistance to ethionine were obtained in the ratio of several cells per $10^5$ cells. The any resistant cells showed requirments of tryptophane and histidine, and were DKD-5D-H strain carring hybrid plasmid prepared from YEp 13. As to 25 colonies among the obtained resistant cells, each colony was cultured in 50 ml of SD+TH medium containing 20 mM L-methionine. Each SAM content was measured to find that the colonies can be classified into at least 2 classes. In the most part (18 colonies), SAM contents in cells were remarkably suppressed and were not more than 2 mg/g of dried cells (hereinafter referred to as "class 1"). However, in several colonies (7 colonies), SAM contents in cells were remarkably enhanced and were not less than 180 mg/g of dried cells (hereinafter referred to as "class 2"). Besides, in DKD-5D-H strain transformed with YEp 13 itself (hereinafter referred to as "DKD-5D-H/YEp 13") as a blank, the SAM content was about 60 mg/g of dried cells.

Figure 1A:
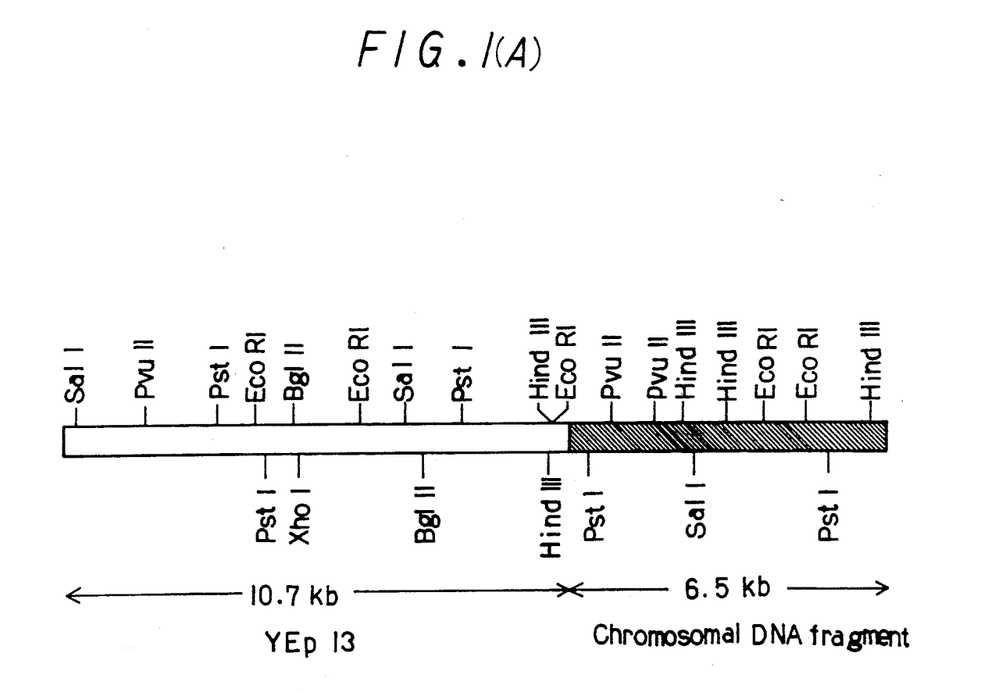
Figure 1B:
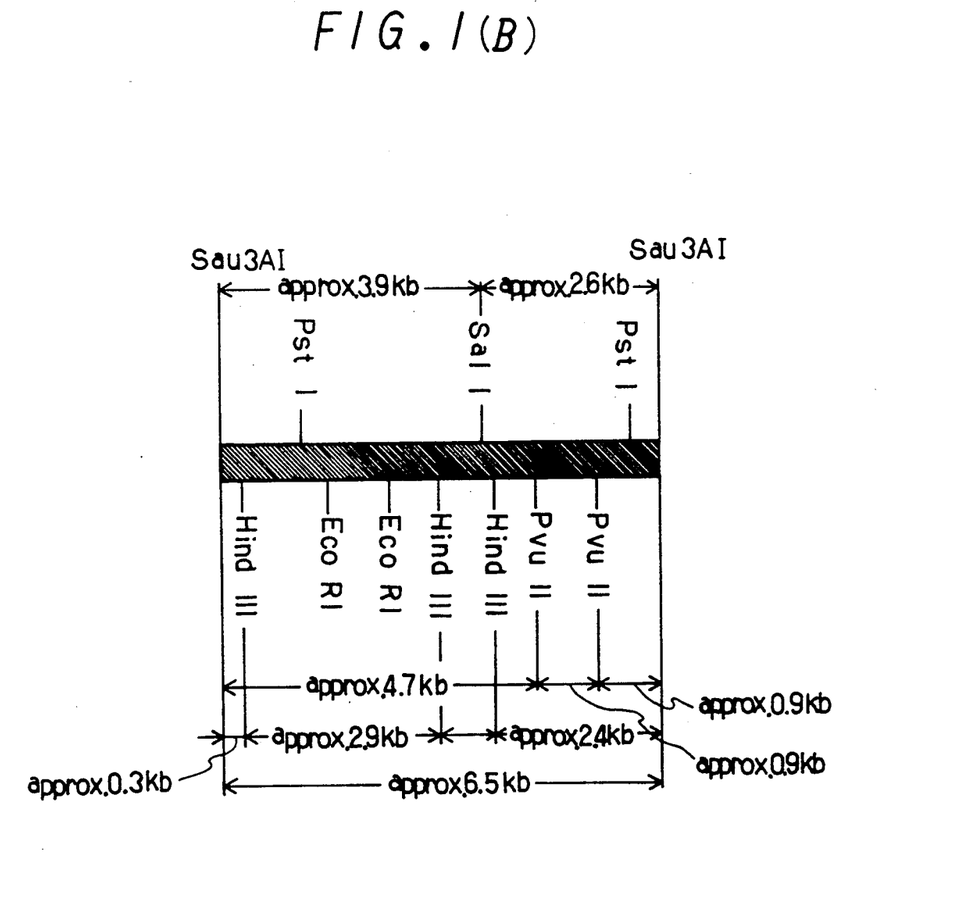

Then, plasmid DNA solution was extracted from transformants belonging to class 2 according to the method of Gunke et al (Journal of Bacteriology, 145, 382-390 (1981)), and was transformed into $E.\ coli$ DH1). That is, transformants of class 2 were cultured while shaking in 1 l of SD+TH medium at 30° C. for one day. After collecting cells by centrifugation at 3000 r.p.m., the collected cells were suspended in a buffer solution (50 mM potassium phosphate buffer solution (pH 8.0), 1M sorbitol and 14 mM mercaptoethanol) so as to contain the cells at 0.2 g of cells/ml. The cell-wall digestion enzyme Zymolyase was added thereto so as to make the enzyme concentration to be 0.1 mg/ml. The obtained mixture was allowed to stand for 1 hour at 30° C. The cells were made to be protoplasts, collected, and suspended in 20 ml of a buffer solution (0.1M citratephosphate buffer containing 0.8M sorbitol and 0.01M EDTA). And thereto was added 2 ml of 10% SDS to disrupt the cells. After 4.2 ml of 5M sodium chloride and then 2-fold volume of cooled ethanol (−20° C.) were addded thereto, the mixture was allowed to stand for 10 hours at −70° C. After that, the precipitate was recovered by centrifugation at 10000 r.p.m., the precipitate was dissolved in a small amount of Tris-EDTA buffer solution and a plasmid solution was obtained. The plasmid solution was transformed into $E.\ coli$ DH1 by means of the above-mentioned method of Cohen et al. Growing cells in an agar plate of L-medium containing ampicillin were purified in the same manner as in the above purification of YEp 13. The obtained plasmids were suitably cleavaged with restriction enzymes, and were subjected to agarose gel electrophoresis, and a restriction enzyme map was made. One of the obtained plasmid (hereinafter referred to as "pYSMH1") is shown in FIG. 1.

SAM in a cell was analyzed according to the following manner. After collecting cultured cells by centrifugation at 3000 r.p.m., the cells were extracted with 10% perchloric acid for 1 hour at 30° C. The supernatant was separated by centrifugation at 10000 r.p.m. for 30 minutes, and then the residue was diluted with 10% perchloric acid so as to make the total amount 5 ml. SAM in the dilution was analized by high performance liquid chromatography (hereinafter referred to as "HPLC"). Analysis conditions of HPLC were, column: GS-320 (made by Asahikasei Co., Ltd.) 76ID-500 mmL, mobile phase: 0.1M sodium phosphate-sodium hydroxide buffer solution (pH 10.0), flow rated: 2.0 ml/min and detection: UV 260 nm.

EXAMPLE 2

The hybrid plasmid-DNA mixture ("solution A" described in Example 1) was transformed into yeast cells of DKD-5D-H strain by a method using an alkali metal described in Example 1. The obtained yeast cells were directly distributed in an agar plate of SD+TH medium containing 50 mg/l ethionine without the step of growing cells once in SD+TH medium. Four days after, each of the obtained twenty strains of resistant cells was cultured in 50 ml of SD+TH medium containing 0.3 mM L-methionine. The SAM contents were measured to find that all the obtained colonies were belonging to class 1, that is, SAM contents in cells were remarkably suppressed and were not more than 2 mg/g dried cells. Also, pYSMH 1 was transformed into yeast cells of DKD-5D-H strain by the method using an alkali metal described in Example 1, the obtained yeast cells were directly distributed in an agar plate of SD+TH medium containing 50 mg/l ethionine without the step of growing cells once in SD+TH medium. No cell grew (at least for two weeks).

EXAMPLE 3

By means of the method with using an alkali metals descried in Example 1, pYSMH 1 and YEp 13 purified in Example 1 were respectively transformed into yeast cells of DKD-5D-H. The yeast cells were distributed in SD+TH agar media, and transformants were obtained. Hereinafter, yeast of DKD-5D-H into which pYSMH 1 was transformed is referred to as "DKD-5D-H/pYSMH 1", and yeast of DKD-5D-H into which YEp 13 was transformed is referred to as "DKD-5D-H/YEp 13". The above-mentioned transformants were studied as to their resistances to ethionine, selenomethionine, methionine ethyl ester, ethionine ethyl ester, which were methionine derivatives. The growth rates of DKD-5D-H/pYSMH 1 were 6 to 10 times faster than those of DKD-5D-H/YEp 13. That is, DKD-5D-H/pYSMH 1 showed resistance to methionine derivatives. Also, DKD-5D-H/pYSMH 1 showed resistance to a high concentration of methionine derivatives.

Figure 2:
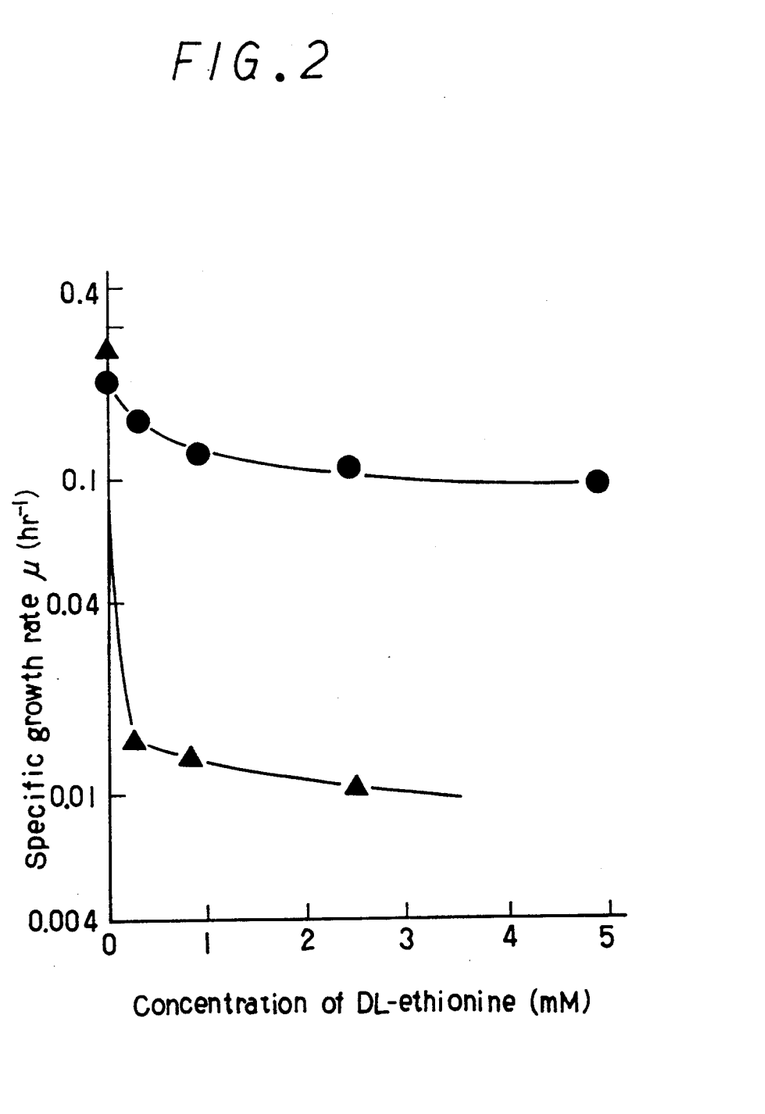
FIG. 2 is a graph showing resistance to ethionine of a transformed cell.
Figure 3:
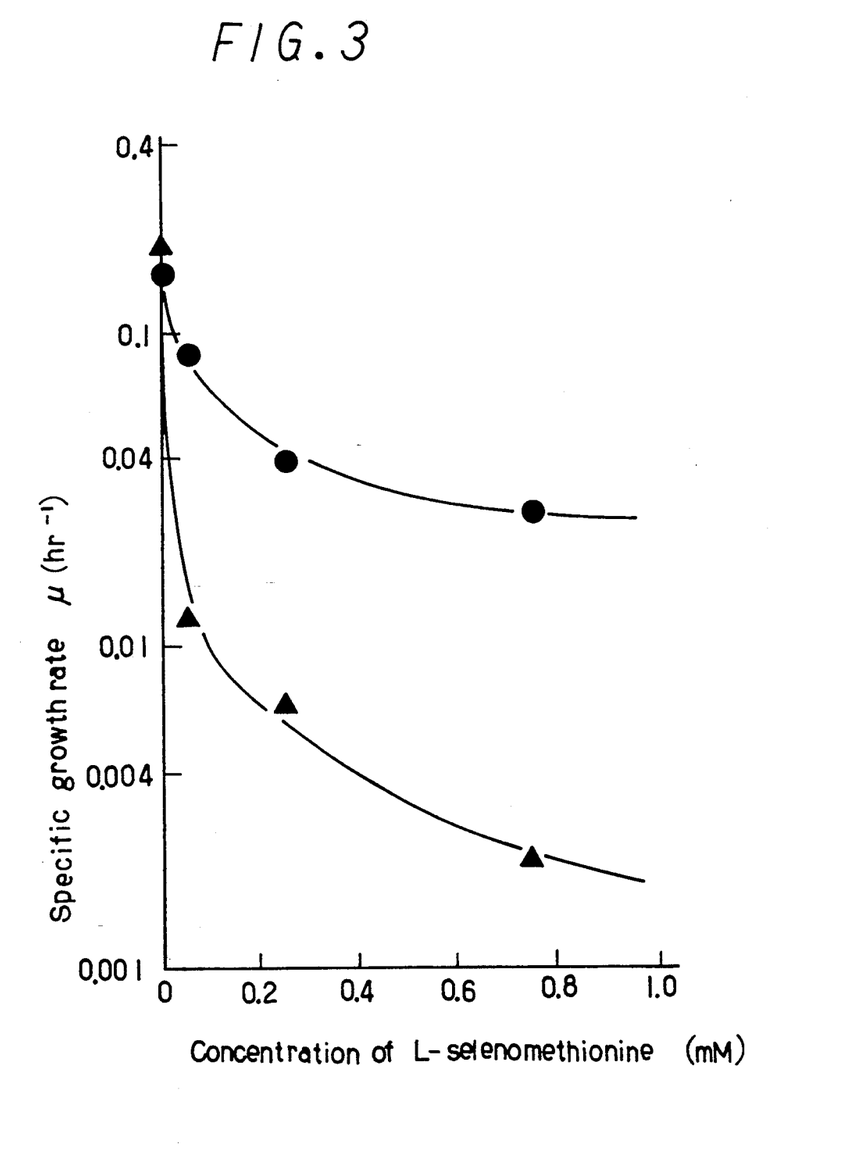
FIG. 3 is a graph showing resistance to selenomethionine of a transformed cell.

As examples, their resistance to DL-ethionine is shown in FIG. 2. Their resistance to L-selenomethionine is shown in FIG. 3. In FIGS. 2 and 3,   and   represent DKD-5D-H/pYSMH 1 and DKD-5D-H/YEp 13, respectively. The cross axis shows a concentration of methionine derivatives in a medium, and the vertical axis shows a specific growth rate.

EXAMPLE 4

Figure 4:
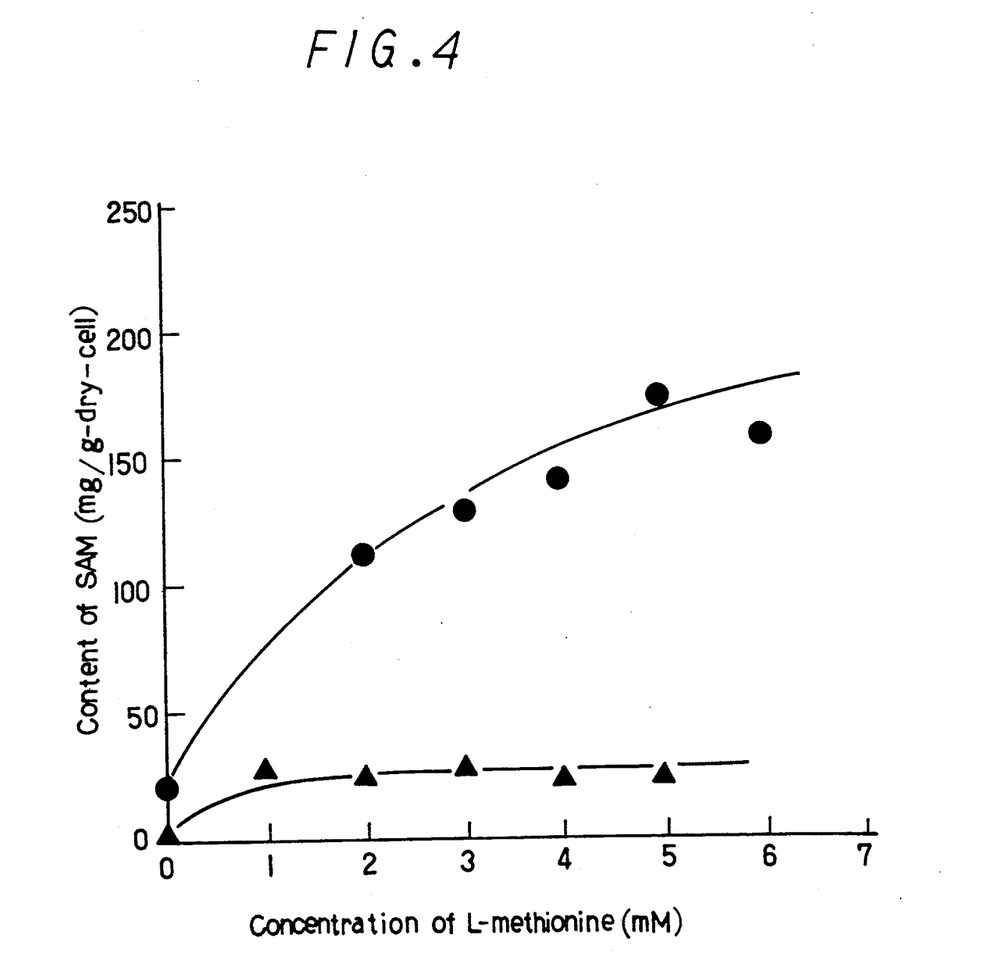
FIG. 4 is a graph showing SAM content in a cell when transformed cells are cultured in a medium added with methionine at various concentrations.

DKD-5D-H/pYSMH 1 and DKD-5D-H/YEp 13 were cultured while shaking in 100 ml of SD+TH media both containing 0 to 5 mM L-methionine, respectively. At late logarithmic growth phase, cells were collected and SAM contents thereof were analyzed. The results are shown in FIG. 4. As a weight of cells, the weight of cells dried at 105° C. for 6 to 8 hours after centrifuging medium containing cells at 3000 r.p.m. and washing once with water (hereinafter referred to as "dry-cell") was used. In FIG. 4,   and   represent DKD-5D-H/pYSMH 1 and DKD-5D-H YEp 13 respectively, the cross axis shows a concentration of methionine in a medium, and the vertical axis shows a weight of SAM contained in cells per weight of dry-cells. As a result, it was found not only that, when a medium contained no methionine, DKD-5D-H/pYSMH 1 was able to accumulate 20 mg/g-dry-cell of SAM, but also that, when a medium contained only 5 mM methionine, DKD 5D-H/pYSMH 1 was able to accumulate 180 mg/g-dry-cell of SAM. Also, outside the cells, there were found SAM in an amount of 5% of total weight of SAM in cells, and the concentration of SAM outside the cells of DKD-5D-H/pYSMH 1 was higher than of DKD-5D-H/YEp 13. Further, when the medium containing 5 mM methionine, DKD-5D-H/pYSMH 1 produced S-adenosyl-L-homocysteine in an amount of about one tenth by weight of SAM, that is, 20 mg/g-dry-cell, which was about ten times large amount in comparison with that of DKD-5D-H/YEp 13. For a comparison, sake yeast IFO 2346 which is said to have a high SAM content, (Shiozaki et al, Agric. Biol. Chem. 48, 2293 (1984)) were cultured in SD medium (2 % glucose, 0.67 % yeast nitrogen base w/o amino acid) containing 5 mM L-methionine. As a result, the sake yeast accumulated 86 mg/g-dry-cell of SAM. That is, SAM content of DKD-5D-H/pYSMH 1 was higher than that of sake yeast IFO 2346.

EXAMPLE 5

DKD-5D-H/pYSMH 1 cells obtained in Example 1 were cultured in SD+TH medium containing 50 μg/ml ethionine. When the weight of dry cells reached 400 mg/l by weight, the culture was stopped. After collecting the cells, the analysis of SAM was carried out in the same manner as in Example 1. As a result, total amount of SAM and S-adenosyl-L-ethionine (hereinafter referred to as "SAE") accumulated in the cells was 410 mg/g-dry-cell.

EXAMPLE 6

Plasmid pYSMH 1 obtained in Example 1 was transformed into sake yeast of S. cervisiae IFO 2346 and IFO 2376, and baker's yeast of S. cervisiae IFO 2044 by the method using an alkali metal (the same method as in Example 1). The obtained yeast cells were distributed in SD agar media. Three days after, growing colonies were collected, they were distributed in a ratio of about 105 cells per plate in agar plates of SD medium containing 500 mg/l DL-ethionine. As a result, since baker's yeast itself had a high resistance to ethionine, the baker's yeast was able to grow even in an agar plate of SD medium containing 500 mg/l DL-ethionine. Therefore, in this concentration, transformed cell was not able to be selected. However, in sake yeast, three days after, only transformed cells were obtained from both media containing 100 mg/l ethionine and 500 mg/l ethionine, respectively. Hereinafter IFO 2346 transformed with pYSMH 1 is referred to as "IFO 2346/pYSMH 1" and IFO 2376 transformed with pYSMH 1 is referred to as "IFO 2376/pYSMH 1". IFO 2346/pYSMH 1 and IFO 2376/pYSMH 1 were transformed into E. coli DH 1 in the same manner as in Example 1. Plasmid DNA from obtained transformants was examined by means of agarose gel electrophoresis according to the alkali rapid method (Journal of Bactriology 145, 1365-1373 (1981)). The position of plasmid band corresponds to that of pYSMH 1 band, thus in sake yeast the gene perticipating in a resistance to methionine derivatives was able to express. Particularly, since IFO 2376 itself had a low resistance to methionine derivatives, cells transformed with plasmid pYSMH 1 was able to be very distinctly selected. IFO 2376 and IFO 2376/pYSMH 1 were cultured in 50 ml of SD medium containing 5 mM L-methionine. The culture was stopped at late logarithmic growth phase (OD: 2.0), after collecting cells, SAM content in cells was measured in the same manner as in Example 1. As a result, SAM content of IFO 2376 was higher than that of IFO 2346 (refer to Example 4), and was 98 mg/g-dry-cell. Further, SAM content of IFO 2376/pYSMH 1 was higher than that of IFO 2376, and was 190 mg/g-dry-cell. At the point when the above measurement was carried out, the plasmid maintaining ratio of IFO 2376/pYSMH 1 was not less than 50% and not more than 80%.

EXAMPLE 7

DKD-5D-H/pYSMH 1 cells obtained in Example 1 were cultured in SD+TH medium containing 5mM L-methionine at late logarithmic growth phase, this culture broth (10 l) containing about 2.5 g of total SAM, was prepared according to the method of Shiozaki et al (Agricultural Biological Chemistry, 48, 2293-2300 (1984)). That is, the cells were harvested by centrifugation and washed with water. SAM was extracted with 10% perchloric acid (100 ml) for 1 hour at room temperature. The sediments were separated off by centrifugation. The supernatant was adjusted to pH 4.5 with 1M potassium hydrogen carbonate under cooling and stirring. After standing the mixture at 4° C. for 30 min, insoluble materials were removed by filtration. The filtrate was applied to a column of Amberlite IRC-50 (H+, 6.5×80 cm, made by Rohm & Haas Co., Ltd.). The column was washed with water until the effluent showed an absorbance of less than 0.2 at 258 nm. Then elution was continued with 0.1 N sulfuric acid. The eluates with an absorbance of more than 0.65 at 258 nm (450 ml) were pooled and put into 2.0 liters of cold acetone. The precipitates were collected by centrifugation, washed with cold acetone, dissolved in a small volume of distilled water and lyophilized to give a white powder (yield: about 1.2 g). HPLC analysis showed that the powder contained 3.2 mmol of SAM (80% by weight, calculated as SAM+ HSO$_4^-$), this powder was further purified on a column of Amberlite IRC-50 (H+, 1.6×15 cm, made by Rohm & Haas Co., Ltd.) in a similar way to as described above.

In addition to the ingredients used in the Examples, other ingredients can be used in the Examples as set forth in the specification to obtain substantially the same results.

What we claim is:

1. An isolated gene functioning in a yeast cell which provides resistance to at least one methionine derivative, is capable of enhancing accumulation of S-adenosyl-L-methionine and has restriction enzyme recognition sites as depicted in FIG. 1(B).

2. A plasmid which includes a gene providing resistance in a yeast cell to at least one methionine derivative and is capable of enhancing accumulation of S-adenosyl-L-methionine, said gene having restriction enzyme recognition sites as depicted in FIG. 1(B).

3. The plasmid of claim 2, wherein said plasmid is pYSMH1 as depicted in FIG. 1(A).

4. A cell transformed with the plasmid of claim 2.

5. The cell of claim 4, wherein said cell is a yeast.

6. The cell of claim 5, wherein the yeast is Saccharomyces cerevisiae.

7. A process for producing S-adenosyl-L-methionine which comprises:
 (i) culturing a yeast cell transformed with a plasmid of claim 2 to accumulate S-adenosyl-L-methionine, and
 (ii) collecting said accumulated S-adenosyl-L-methionine.

* * * * *